United States Patent
Davis

(10) Patent No.: US 8,572,610 B2
(45) Date of Patent: Oct. 29, 2013

(54) PATIENT MONITORING SYSTEM AND METHOD OF SAFE OPERATION WITH THIRD PARTY PARAMETER APPLICATIONS

(75) Inventor: Carl C. Davis, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 605 days.

(21) Appl. No.: 12/634,381

(22) Filed: Dec. 9, 2009

(65) Prior Publication Data
US 2011/0138386 A1    Jun. 9, 2011

(51) Int. Cl.
G06F 9/455    (2006.01)
G06F 9/46    (2006.01)
G06F 13/28    (2006.01)
G06F 13/00    (2006.01)

(52) U.S. Cl.
USPC ................. 718/1; 718/104; 710/21; 710/100; 719/321; 719/322; 719/323; 719/324

(58) Field of Classification Search
USPC ........... 718/1–105; 719/321–327; 710/20–21, 710/36–38, 100
See application file for complete search history.

(56) References Cited

U.S. PATENT DOCUMENTS

| | | | |
|---|---|---|---|
| 6,944,847 B2 | 9/2005 | Desai et al. | |
| 7,797,699 B2 * | 9/2010 | Kagi et al. | 718/1 |
| 8,200,796 B1 * | 6/2012 | Margulis | 709/223 |
| 8,464,260 B2 * | 6/2013 | Riley | 718/101 |
| 2004/0193070 A1 * | 9/2004 | Schilder et al. | 600/558 |
| 2005/0076324 A1 * | 4/2005 | Lowell et al. | 717/100 |
| 2005/0251806 A1 | 11/2005 | Auslander et al. | |
| 2006/0069828 A1 * | 3/2006 | Goldsmith | 710/100 |
| 2008/0104590 A1 * | 5/2008 | McCrory et al. | 718/1 |
| 2008/0123676 A1 | 5/2008 | Cummings et al. | |
| 2008/0126614 A1 * | 5/2008 | Ooi et al. | 710/38 |
| 2008/0162800 A1 | 7/2008 | Takashige et al. | |
| 2009/0049493 A1 | 2/2009 | White et al. | |
| 2009/0222558 A1 | 9/2009 | Xu et al. | |
| 2012/0139927 A1 * | 6/2012 | Vembu et al. | 345/502 |

OTHER PUBLICATIONS

Frank Shen, "Designing Robust Wireless Sensor Applications", Oct. 1, 2009, Medical Electronics Design. Web address: http://www.medicalelectronicsdesign.com/article/designing-robust-wireless-sensor-applications [Accessed Feb. 23, 2011].

(Continued)

Primary Examiner — Abdullah Al Kawsar
(74) Attorney, Agent, or Firm — Andrus, Sceales, Starke & Sawall, LLP

(57) ABSTRACT

The system and method of the present application includes a functional software stack including a type 1 hypervisor running on a single hardware platform. One embodiment of the hardware platform includes a processor and storage media, as well as network and video hardware. The hypervisor includes a network driver and a display driver, and executes directly on the hardware and abstracts the hardware from any guest operating systems (OS). To the OS, the hypervisor appears to be the base hardware platform and the network and display drivers appear to be similar hardware as well. The guest OS includes the resident patient monitoring application as well as third party applications, both of which execute independently on the virtualized hardware of the hypervisor. The network and display drivers manage the monitoring network and display regions in a monitoring display that are available to the guest operating systems.

10 Claims, 2 Drawing Sheets

(56) References Cited

OTHER PUBLICATIONS

Tanveer Alam, "Maximizing Service Uptime with intel® Virtualization Technology and Intel® Active Management Technology Inside Your Embedded System", Oct. 2009, Intel Corporation, Web Address: http:/download.intel.com/design/intarch/papers/322684.pdf [Accessed Feb. 23, 2011].

Barham et al., "Xen 2002". Jan. 9, 2003. University of Cambridge Computer Laboratory. ISSN 1476-2986. Web Address: http://www.cl.cam.ac.uk/techreports/UCAM-CL-TR-553.pdf [Accessed Feb. 23, 2011].

Intel Technology Journal, vol. 10, Issue 3, Aug. 10, 2006, pp. 179-192. pp. 180-181. ISSN 1535-864X. Web Address: http://download.intel.com/technology/itj/2006/v10i3/v10-i3-art02.pdf [Accessed Feb. 23, 2011].

GB Search Report from corresponding GB Application No. GB1020612.6 on Mar. 1, 2011.

\* cited by examiner

US 8,572,610 B2

PATIENT MONITORING SYSTEM AND METHOD OF SAFE OPERATION WITH THIRD PARTY PARAMETER APPLICATIONS

FIELD

The present application is directed to the field of patient monitoring systems. More specifically, the present application is directed to the field of patient monitoring system compatibility with third party systems.

BACKGROUND

In current monitoring systems, when new or hospital specific parameters are added to the monitoring system, a new parameter and functional logic needs to be developed and integrated in the core monitoring software. Current systems include a level of control and scrutiny required during development to ensure primary alarm function is not jeopardized by new software. This results in long delays between the release of new parameter modules, and/or a monitor that can display that parameter. In addition, specialty parameter devices or research devices for these new parameters are rarely introduced due to the limited market opportunity.

Other current monitoring systems attempt to translate protocols. As long as the monitoring system already understands a base parameter, new third party devices can be supported in this solution. For example, a new third party blood oxygen level (SpO2) parameter is available if SpO2 is already displayed at the monitor. This type of system and method does not address the need to have new classes of parameters available on the monitor, i.e., in this current monitoring system, monitor code still needs to be modified, and does not allow for third party application code to run.

Further current monitoring systems utilize running multiple independent processes or including two physical processing elements to segregate the monitoring application and non-secure application. Obviously, this solution requires additional hardware, making it less efficient, more expensive and more cumbersome.

SUMMARY

The system and method of the present application includes a functional software stack including a type 1 hypervisor running on a single hardware platform. One embodiment of the hardware platform includes a processor and storage media, as well as network and video hardware. The hypervisor includes a network driver and a display driver, and executes directly on the hardware and abstracts the hardware from any guest operating systems (OS). To the OS, the hypervisor appears to be the base hardware platform and the network and display drivers appear to be similar hardware as well. The guest OS includes the resident patient monitoring application as well as third party applications, both of which execute independently on the virtualized hardware of the hypervisor. The network and display drivers manage the monitoring network and display regions in a monitoring display that are available to the guest operating systems.

A patient monitoring system, the system comprising a hardware platform, wherein the hardware platform includes a processor and a storage medium, wherein a set of executable code is stored on the storage medium and executed by the processor, a hypervisor configured on the hardware platform, the hypervisor including a network driver and a display driver, wherein operation of the hypervisor is effectuated by the executed code, a secured operating system, and a third party operating system, wherein each of the secured operating system and third party operating system communicates independently with the network driver and the display driver such that the secured and third party operating systems are separately operable with the patient monitoring system.

A patient monitoring system, the system comprising a hardware platform, wherein the hardware platform includes a processor and a storage medium, wherein a set of executable code is stored on the storage medium and executed by the processor, effectuating the operation of the hypervisor, a hypervisor configured on the hardware platform, the hypervisor including a network driver and a display driver, wherein operation of the hypervisor is effectuated by the executed code, a secured operating system, and a third party operating system, wherein each of the secured operating system and third party operating system communicates independently with the network driver and the display driver such that the secured and third party operating systems are separately operable with the patient monitoring system.

A method of safely operating a patient monitoring system with a third party application, the method comprising configuring a hardware platform with a processor and a storage medium, executing a set of executable code stored on the storage medium, effectuating the operation of a hypervisor, and further wherein the hypervisor is configured on the hardware platform, and the hypervisor includes a network driver and a display driver, coupling a secured operating system with the hypervisor, and coupling a third party operating system with the hypervisor, wherein each of the secured operating system and third party operating system communicates independently with the network driver and the display driver such that the secured and third party operating systems are separately operable with the patient monitoring system.

DETAILED DESCRIPTION

Figure 1:
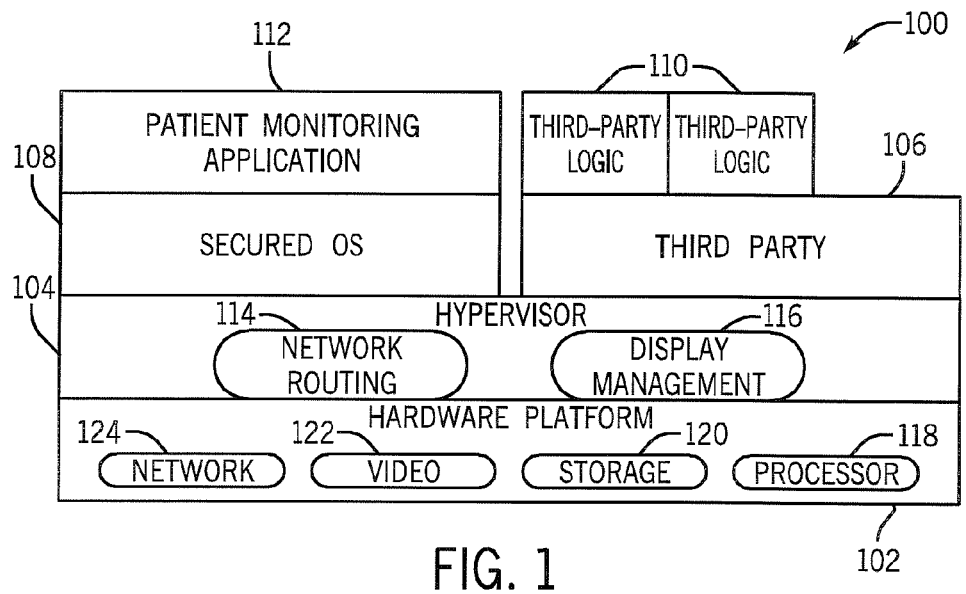
FIG. 1 is a schematic block diagram illustrating an embodiment of a portion of a monitoring system of the present application.

An embodiment of a monitoring system 100 of the present application is illustrated in FIG. 1. For ease of explanation, FIG. 1 includes a focused view of the elements of the monitoring system 100 of the system and method of the present application. In other words, it is important to note that a monitoring system 100 including the system and method of the present application, may also include a further number of devices and elements not shown in FIG. 1, or the rest of the figures included in this application. Such additional elements may include, but are not limited to, devices for the collection of physiological parameters of a patient, connectors and/or wired or wireless transmissions systems capable of relaying the physiological parameters of a patient from the collection devices to the monitoring system 100, additional displays as needed, and any other modules or hardware items utilized in any known or future monitoring systems 100.

Referring again to FIG. 1, a hardware platform 102 includes a processor 118, a storage medium 120, video hardware 122, and network hardware 124. Computer code utilized to perform the operation of the monitoring system 100 is stored on the storage medium 120 and executed by the processor 118. Video hardware 122 effectuates the display of the physiological parameters of a patient, and the network hardware 124 provides a connection to any other systems that the patient monitoring system 100 is connected with. For example, the network hardware 124 may effectuate connection to any internal hospital or clinical system such as, but not limited to, electronical medical record (EMR) or clinical information systems (CIS). The network hardware 124 and the network driver 114, which will be described below, further is the pathway through which data is received into the monitoring system 100, as well as how the monitoring system 100 is connected with other monitors and other hardware devices as well.

Still referring to FIG. 1, a hypervisor 104 including a network driver 114 and a display driver 116 is implemented on the hardware platform 102. Preferably, the hypervisor is a type 1 hypervisor, that is a software system configured to run directly on the hardware platform 102 as a hardware control. As will be discussed later, the guest operating systems (OS) 106, 108 run on another level above the hypervisor, but are managed by the hypervisor nonetheless. The hypervisor 104, sometimes referred to as a Virtual Machine Monitor (VMM) is a computer software/hardware platform virtualization software that allows multiple operating systems to run on a host computer concurrently.

Still referring to FIG. 1, the hypervisor 104 executes directly on the hardware platform 102 and abstracts the hardware platform 102 for any guest operating system 106, 108. For the guest operating systems 106, 108, the hypervisor 104 appears to be the hardware platform 102. Furthermore, the network driver 114 and display driver 116 appear to the guest operating system 106, 108 as actual networking and display hardware (they appear as the video hardware 122 and network hardware 124). These drivers 114, 116 provide functionality to manage regions on any monitoring display (that will be discussed further below) and provide third party code or third party parameter information, that are available to the guest operating systems 106, 108. This allows each of the guest operating systems 106, 108 to execute on the hypervisor 104 entirely independent from one another.

Each of the guest operating systems 106, 108 including the third party operating system 106 and the secured operating system 108 have a corresponding application. The secured operating system 108 includes the resident patient monitoring application 112, and the third party operating system includes the third party application 110. As discussed above, the secured operating system 108 and its patient monitoring application 112 is resident in the monitoring system 100. That is, the normal operation of the patient monitoring application 112 is being run and utilized to collect, process and display physiological parameters of a patient. The secured operating system 108 is a "locked down" operating system and only allows the patient monitoring software or patient monitoring application 112 to be executed. Obviously, this secured OS 108 only runs the resident patient monitoring application 112 and its associated code for the benefit and safety of the patient. Disrupting this patient monitoring application 112 may cause improper monitoring, which could lead to a serious patient condition.

As discussed above in the description of current systems, problems occur when third party applications 110 including third party parameter or code need to be added to the monitoring system 100. This system 100 and method of the present application allows each of the patient monitoring application 112 and third party application 110 to be implemented through by respective guest operating systems, 108, 106 through the hypervisor 104. In additional embodiments, additional third party applications 110 may be added. Such additional third party application 110 cause the third party operating system 106 to divide the available operating space accordingly.

Figure 2:
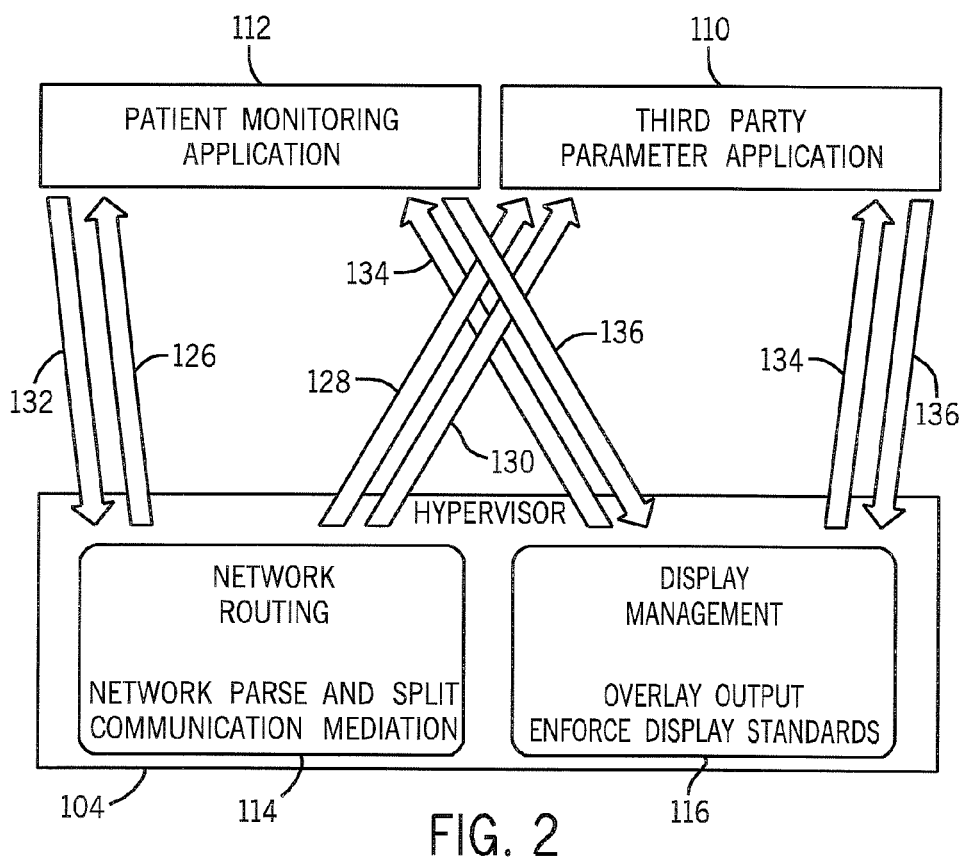
FIG. 2 is a schematic block diagram illustrating an embodiment of a portion of a monitoring system of the present application.

Referring to FIG. 2, in operation, the patient monitoring application 112 and the third party application 110 communicate separately with both of the network driver 114 and the display driver 116 on the hypervisor 104. The patient monitoring application control 132 provides instructions to the network driver 114 with respect to the patient monitoring application's 112 requirements including requirements for display space. The network driver 114 provides a known parameter feed 126 to the patient monitoring application 112 and manages the flow of patient monitoring application 132—including settings and alarm notifications—specific to the patient monitoring application 112. The known parameter feed 126 includes only parameters and information that is currently understood by the existing patient monitoring application 112. The network driver 114 will also provide a parameter subset feed 128 to the third party application 110. This parameter subset feed 128 may include only parameters not recognized as current known parameters of the patient monitoring application 112. In addition, the network driver 114 may pass executable program logic to the third party parameter application 110 for execution. In this way additional application logic may be executed without any possibility of corrupting the operation of the patient monitoring application 112. The display driver 116 will provide a display context feed 134 to each of the applications 112, 110. This display context feed 134 defines the amount of display that each application 112, 110 will have available for each of the applications 112, 110 displayed content. Each application 112, 110 will send back to the display driver 116 a display output feed 136. This display output feed 136 will include the content for display on the monitor. Further, the display driver 116 will publish context appropriate to the particular application 112, 110 and merge the displays. As an example, when an application 112, 110 requests a screen size, this request is reported as a size appropriate to the application 112, 110. In other words, if a 1024×200 block out of a 1280×1024 display is allocated for the third party parameter display area 202 (FIG. 3), the display driver 116 would report a screen size of 1024× 200 to the third party application 110. Please further note that this FIG. 2 has been simplified for clarity by removing the secured operating system 108 and third party operating system 106, but it is understood that these operating systems are still resident in the system 100 in FIG. 2.

Figure 3:
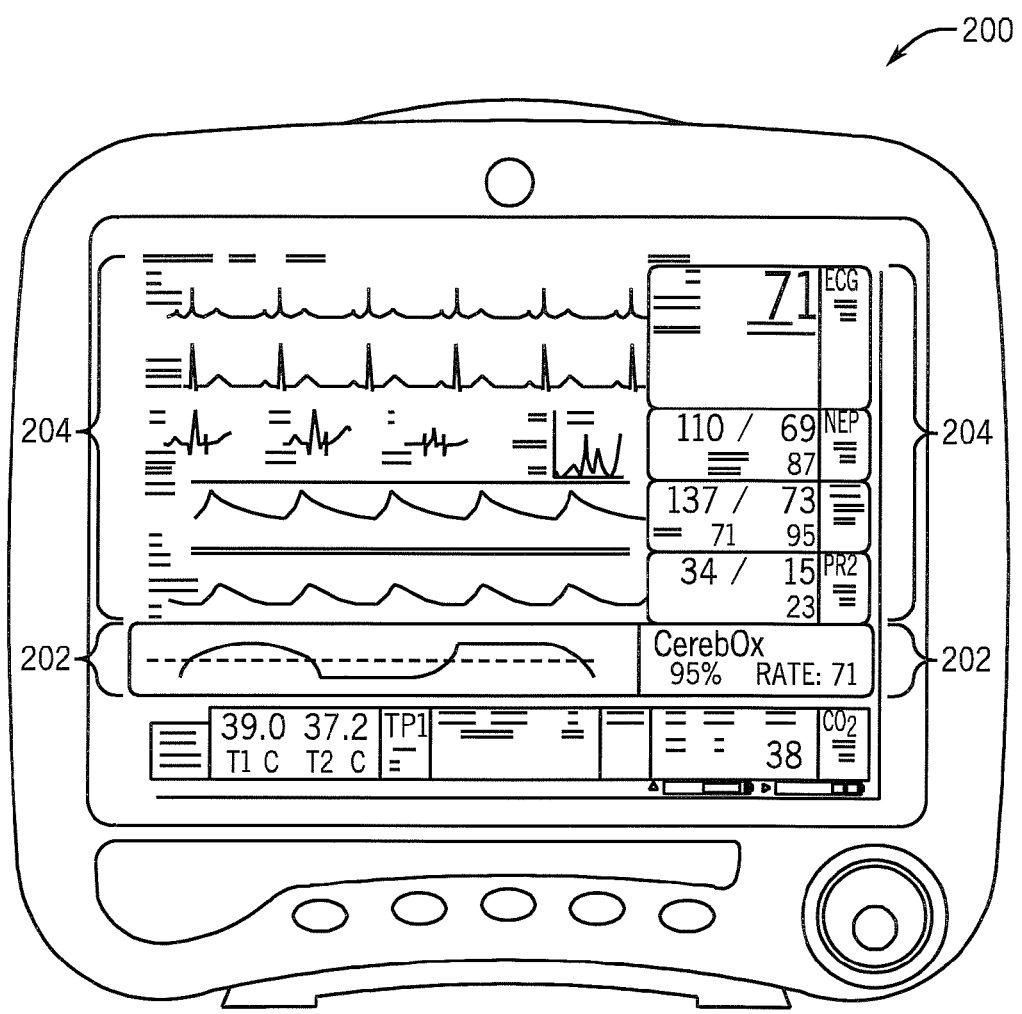
FIG. 3 is a graphical representation illustrating an embodiment of the present application.

Referring now to FIG. 3, an exemplary monitor display unit 200 of the present application is illustrated. Here, the patient monitoring application display area 204 shows display characteristics of the physiological parameters measured and displayed using the patient monitoring application 112 (FIGS. 1 and 2). Again, as discussed above, these parameters displayed in the patient monitoring application display area 204 are resident in the monitoring system 100. The third party parameter display area 202 shows the measured physiological parameter designated by the third party application 110, and the allocated third party parameter display area 202 configured by the display driver 116 in the hypervisor 104. Of course, this monitor display unit is exemplary, as is the third party parameter display area 202. The monitor display unit 200 may be of varying size, including any unit capable of operating with the operating system 100. Furthermore, the third party parameter display area 202 is dependent upon the needs of the patient monitoring application 112, and those of the third party application 110, as discussed above with respect to FIG. 2. In other words, the third party parameter display area 202 may be larger or smaller and be configured in other portions of the monitor display unit 200, according to the requirements of each application 112, 110.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A patient monitoring application for safe operation with a third party application, the system comprising:
    a hardware platform;
    a hypervisor configured on the hardware platform, the hypervisor including a network driver and a display driver; and
    a plurality of guest operating systems, wherein each of the plurality of guest operating systems communicates independently of the remaining plurality of guest operating systems with the network driver and the display driver such that each of the plurality of guest operating systems operates separately from the remaining plurality of guest operating systems with the patient monitoring system,
    wherein the plurality of guest operating system includes a secured operating system, wherein the secure operating system implements a patient monitoring application, wherein the patient monitoring application is displayed in a patient monitoring application display area of a monitor display unit, and further wherein the plurality of guest operating systems includes a third party operating system, wherein the third party operating system implements the third party application, wherein the third party application is displayed in a third party parameter display area of the monitor display unit simultaneously with the patient monitoring application,
    wherein the patient monitoring application provides instruction to the network driver with respect to network parameter requirement of the patient monitoring application and based on the instruction the network driver provides a known parameter feed to the patient monitoring application that is currently understood by the patient monitoring application and also provides a separate parameter subset feed to the third party application that is not recognized by the patient monitoring application, wherein each of the patient monitoring application and the third party application communicates independently with the network driver and the display driver.

2. The system of claim 1, wherein the hardware platform includes video hardware and network hardware, wherein the network driver and display driver facilitate the execution of the plurality of guest operating systems on the video hardware and network hardware.

3. The system of claim 2, wherein the hardware platform further includes a processor and a storage medium, wherein a set of executable code is stored on the storage medium and executed by the processor, effectuating the operation of the hypervisor.

4. The system of claim 1, wherein the hypervisor is a type 1 hypervisor.

5. A patient monitoring system, the system comprising:
    a hardware platform, wherein the hardware platform includes a processor and a storage medium, wherein a set of executable code is stored on the storage medium and executed by the processor;
    a hypervisor configured on the hardware platform, the hypervisor including a network driver and a display driver, and further wherein operation of the hypervisor is effectuated by the executed code;
    a secured operating system; and
    a third party operating system, wherein each of the secured operating system and third party operating system communicates independently of each other with the network driver and the display driver such that the secured and the third party operating systems operate separately from each other with the patient monitoring system,
    wherein the secured operating system implements a patient monitoring application, and the patient monitoring application is displayed in a patient monitoring application display area of a monitor display unit, and further wherein the third party operating system implements a third party application, and the third party application is displayed in a third party parameter display area of the monitor display unit simultaneously with the patient monitoring application,
    wherein the patient monitoring application provides instruction to the network driver with respect to network parameter requirement of the patient monitoring application and based on the instruction the network driver provides a known parameter feed to the patient monitoring application that is currently understood by the patient monitoring application and also provides a separate parameter subset feed to the third party application that is not recognized by the patient monitoring application, wherein each or the patient monitoring application and the third party application communicates independently with the network driver and the display diver.

6. The system of claim 5, wherein the hardware platform includes video hardware and network hardware, wherein the network driver and display driver facilitate the execution of the plurality of guest operating systems on the video hardware and network hardware.

7. The system of claim 5, wherein the hypervisor is a type 1 hypervisor.

8. A method of safely operating a patient monitoring system with a third party application, the method comprising:
    configuring a hardware platform with a processor and a storage medium;
    executing a set of executable code stored on the storage medium, effectuating the operation of a hypervisor, and further wherein the hypervisor is configured on the hardware platform, and the hypervisor includes a network driver and a display driver;
    coupling a secured operating system with the hypervisor;
    coupling a third party operating system with the hypervisor, wherein each of the secured operating system and third party operating system communicates independently of each other with the network driver and the display driver such that the secured and third party operating systems operate separately with the patient monitoring system,
    implementing a patient monitoring application with the secured operating system;
    implementing the patient monitoring application in a patent monitoring display area of a monitor display unit;
    implementing a third party application with the third party operating system; and
    displaying the third party application in a third party parameter display area of the monitor display unit simultaneously with the patient monitoring application, wherein the patient monitoring application provides instruction to the network driver with respect to network parameter requirement of the patient monitoring application and based on the instruction the network driver provides a known parameter feed to the patient monitoring application that is currently understood by the patient monitoring application and also provides a separate parameter subset feed to the third party application that is not recognized by the patient monitoring application, wherein each of the patient monitoring application and the third party application communicates independently with the network driver and the display driver.

9. The method of claim 8, further comprising executing the plurality of guest operating systems on video hardware and network hardware on the hardware platform, wherein the network driver and display driver facilitate the execution of the plurality of guest operating systems on the video hardware and the network hardware.

10. The method of claim 8, wherein the hypervisor is a type 1 hypervisor.

* * * * *